United States Patent [19]
Fraser et al.

[11] 3,948,601
[45] Apr. 6, 1976

[54] STERILIZING PROCESS AND APPARATUS UTILIZING GAS PLASMA

[75] Inventors: Sheila J. Fraser, Seattle; Roger B. Gillette, Auburn; Richard L. Olson, Bellevue, all of Wash.

[73] Assignee: The Boeing Company, Seattle, Wash.

[22] Filed: June 25, 1973

[21] Appl. No.: 373,262

Related U.S. Application Data

[63] Continuation-in-part of Ser. No. 313,954, Dec. 11, 1972, abandoned, which is a continuation-in-part of Ser. No. 207,487, Dec. 13, 1971, Pat. No. 3,851,436.

[52] U.S. Cl............ 21/54 R; 21/102 R; 23/258.5 R
[51] Int. Cl.².......................................... A61L 1/00
[58] Field of Search......... 21/54 R, 102 R; 250/531; 204/165, 193; 23/258.5

[56] References Cited
UNITED STATES PATENTS

| | | | |
|---|---|---|---|
| 3,383,163 | 5/1968 | Menashi | 21/54 R |
| 3,410,776 | 11/1968 | Bersin | 204/193 |
| 3,428,548 | 2/1969 | Hollahan | 250/531 |
| 3,600,126 | 8/1971 | Hellund | 21/102 R |
| 3,701,628 | 10/1972 | Ashman et al. | 21/54 R |

*Primary Examiner*—Morris O. Wolk
*Assistant Examiner*—Timothy W. Hagan
*Attorney, Agent, or Firm*—Robert W. Beach

[57] ABSTRACT

A continuous flow of gas plasma is supplied to a space at a very low pressure in which the object to be sterilized is located. Cool plasma of a suitable gas such as argon is produced continually by being subjected to a radio-frequency field. Complex shapes such as capillary passages through a blood oxygenator can be sterilized by passing the gas plasma through them. The exterior of objects to be sterilized can be subjected to gas plasma in a space at a very low pressure either confined or unconfined. The space may, for example, be a packaging envelope, and subsequent to sterilization such envelope can be evacuated and collapsed onto the object to preserve its sterile character.

18 Claims, 4 Drawing Figures

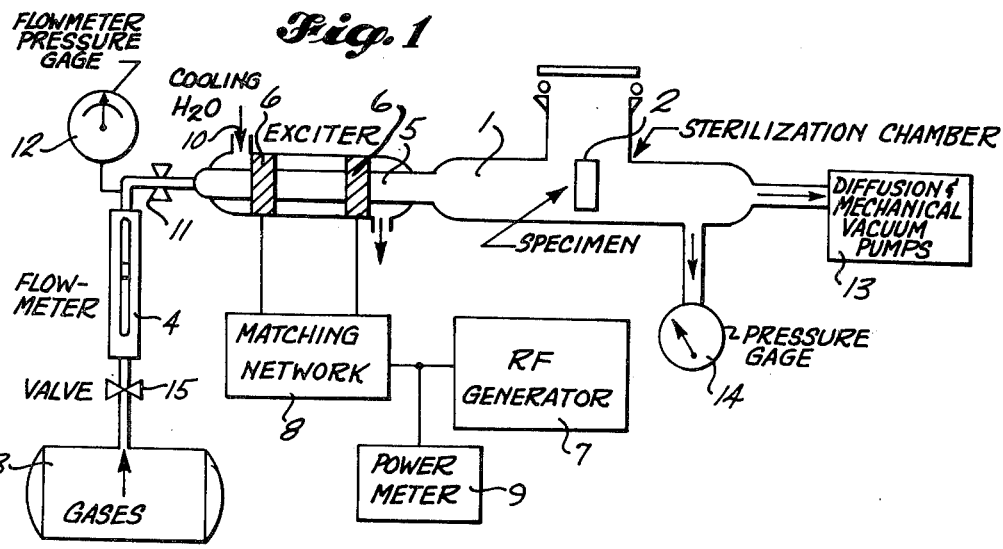
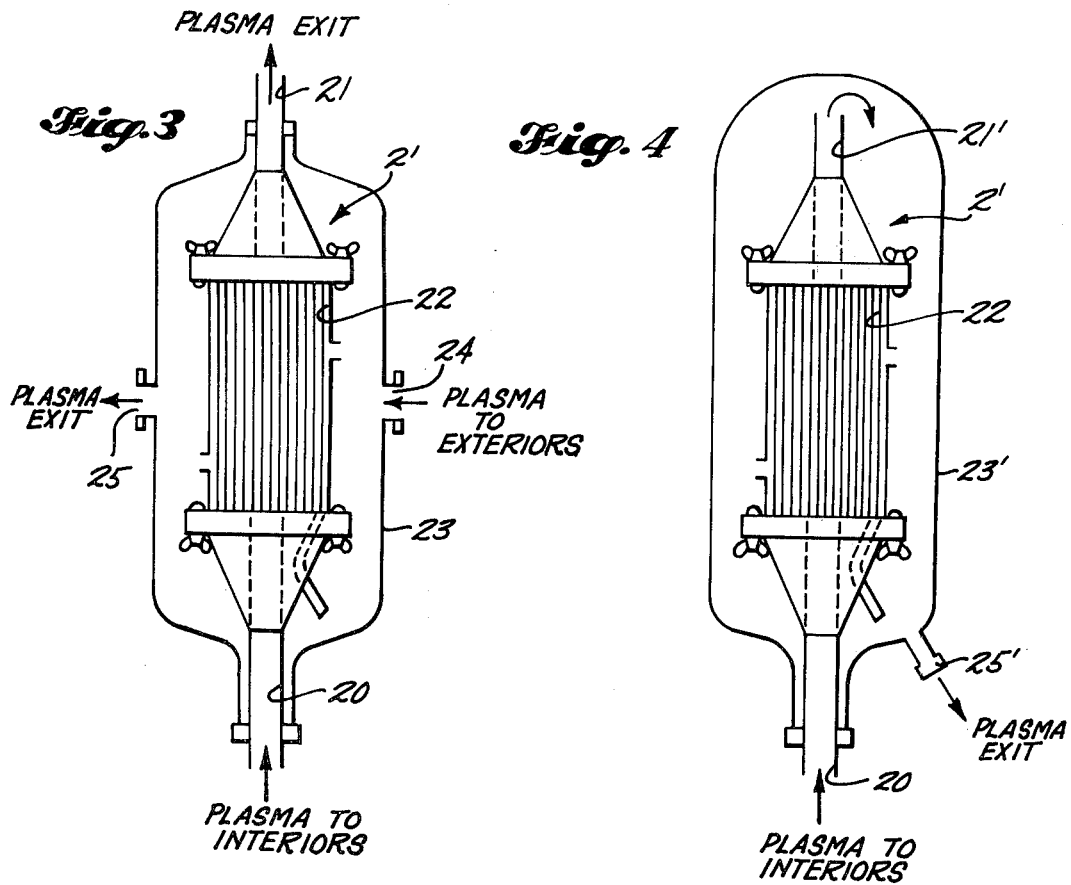

STERILIZING PROCESS AND APPARATUS UTILIZING GAS PLASMA

This application is a continuation-in-part of abandoned application Ser. No. 313,954, filed Dec. 11, 1972, entitled Sterilizing Process and Apparatus Utilizing Gas Plasma, which is a continuation-in-part of application Ser. No. 207,487, filed Dec. 13, 1971 now U.S. Pat. No. 3,851,436, entitled Sterilizing and Packaging Process Utilizing Gas Plasma.

This invention relates to the sterilization by the use of cool gas plasma of various types of articles, including articles sufficiently fragile so that they cannot be subjected to a high pressure differential or which are made of material that will become plastic or melt at high temperatures, or which would be damaged if subjected to thermal shock by an abrupt temperature change.

A principal object of the present invention is to provide a sterilizing process and apparatus in which the sterilizing effectiveness of gas plasma is increased by providing a continued flow of the gas plasma over surfaces to be sterilized with minimum dilution by air.

A further object is to provide apparatus by which gas plasma will be brought most effectively into contact with surfaces to be sterilized.

Another object is to cover immediately surfaces which have been sterilized by flow of gas plasma over them so as to preserve their sterile character.

FIG. 1 is a diagram of representative sterilizing apparatus utilizing gas plasma according to the present invention.

FIG. 3 and FIG. 4 are detail elevations of somewhat modified portions of the apparatus shown in FIG. 2.

Figure 2:
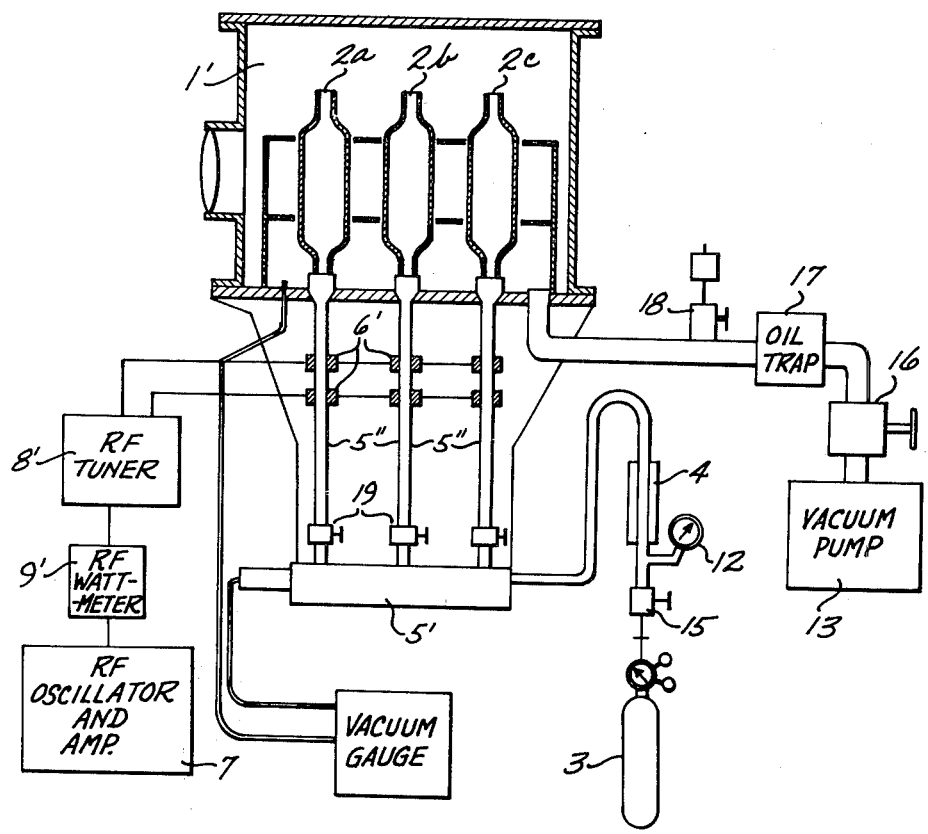
FIG. 2 is a diagram of another type of sterilizing apparatus using the plasma process of the present invention, parts being shown in section.

Sterilization of articles by the process of the present invention is accomplished in a space at a very low pressure such as from 50 to 3,000 microns. Such space may be either confined such as within a sterilization chamber, or may be unconfined such as in the rarified atmosphere of outer space. In the apparatus illustrated in the present application the closed sterilization chamber 1 houses an article 2 to be sterilized. Such article is inserted into such chamber through a suitable aperture closable to withstand substantial external pressure. Preferably the chamber is provided in a casing of cylindrical shape which can be evacuated without collapsing. The apparatus, including the casing, can be metal, but it may be preferable for part or most of the components to be made of glass or suitable plastic material.

Gas suitable for ionizing into the form of plasma to be supplied to the chamber 1 includes argon, nitrogen, oxygen, helium, and xenon but preferably is a nonoxidizing gas. Mixtures of these gases may also be used to improve sterilization efficiencies. The preferred gas for such use is argon. The gas from which the plasma is produced is supplied from a tank 3 in which it is stored under pressure through a flowmeter 4 to the plasma production conduit 5 connected to one end of the sterilization chamber 1. Such plasma-production conduit is subjected to a radio-frequency field created by the electrodes 6, which may encircle such conduit. The shape of such electrodes is not critical and they may be simply of rectangular shape. The size of the electrode plates depends on the power of the radio-frequency generator and the spacing between the plates.

Condenser plates have been placed on opposite sides of a 3-inch diameter cylindrical quartz tube having 4-inch widths extending lengthwise of the tube and 2-inch widths extending circumferentially of the tube and connected to a radio-frequency power source of 50 to 300 watts. Alternatively collars 1-inch wide encircling the tube and spaced apart 2-½ inches to 3 inches have been connected to the circuit. On a smaller quartz tube about ½ inch in diameter, collars 1 inch in width and spaced apart 1 inch were connected to the radio-frequency power source of 25 to 200 watts. A suitable radio-frequency generator 7 is connected to the electrodes 6 through an impedance matching network 8 for coupling the capacitive electrodes 6 to an amplifier of the radio-frequency generator 7. The oscillator and amplifier of the radio-frequency generator should be capable of producing up to 300 watts of continuous power as indicated by the power meter 9. A preferred output of the radio-frequency generator is 200 watts. A preferred frequency is 13.56 megahertz, but frequencies in the range of 3 to 30 megahertz are satisfactory.

It may be desirable to cool the plasma generator conduit 5 by passing cooling water or other coolant through the cooling jacket 10. The supply of gas to the plasma generator can be regulated by a valve 11, and measured with the flowmeter 4. The flowmeter pressure gauge 12 is used to maintain the proper pressure in the flowmeter. The quantity of gas flow can be from 2 to 50 cubic centimeters per minute. A volume of 18 cubic centimeters per minute is sufficient for operating sterilizing apparatus of convenient size.

The quantity of gas plasma flowing through the sterilization chamber 1 is determined, not only by the flowmeter 4 and the valve 11, but also by the pressure in the sterilization chamber 1 through which the plasma flows. The pressure in such sterilization chamber is preferably quite low, not exceeding a few millimeters of mercury. The pressure should be within the range of 0.05 to 3 millimeters of mercury, i.e., from 50 to 3,000 microns, and a preferred pressure is 200 microns. The pressure in the sterilization chamber could be indicated by a pressure gauge 14.

The supply of gas to the plasma generator from the tank 3 can be controlled by a shutoff valve 15. When it is desired to use the apparatus, the article to be sterilized is placed in the sterilization chamber 1, the vacuum pump 13 is started to evacuate the chamber, and the shutoff valve 15 is opened to enable gas to flow from the storage tank 3 through the flowmeter 4 and regulating valve 11 to the plasma generator 5. It is assumed that the flowmeter 4 and valve 11 have previously been set to supply the desired quantity of gas induced by the suction of pump 13 applied to the sterilization chamber 1. Provision for grounding a portion of the sterilization chamber downstream from the plasma source may also enhance the sterilization efficiency.

The radio-frequency generator 7 is then energized and the impedance matching network 8 is adjusted to minimize reflected power. The article is subjected to the flow over it of the gas plasma passing through the sterilization chamber for the period of time required to effect sterilization. The temperature of the gas plasma when generated may be 100° to 500°C, but by the time the plasma has reached the article to be sterilized it is cool, such as being in the range of 25° to 50°C. Reductions in spore populations as much as 99% have been accomplished by exposure of the article to be sterilized to plasma flow for a period of time as short as 2 minutes. Articles to be sterilized can, however, be subjected continuously to the plasma for a period of time between 1 minute and 6 hours.

When the sterilization of the particular article has been completed, the radio-frequency generator 7 is deenergized, the gas supply valve 15 is closed, and the vacuum pump 13 is stopped or its connection to the sterilization chamber is severed by a suitable valve. The sterilization chamber is then vented to atmosphere, the chamber is opened, and the sterilized object removed from it.

The apparatus shown in FIGS. 2, 3 and 4 is of the type particularly adapted to the sterilization of artificial lung blood oxygenators. Such oxygenators are made of soft silastic material and cellulose acetate hollow fibers. The apparatus preferably is capable of sterilizing several of such oxygenators at the same time, three of such oxygenators, 2a, 2b and 2c, being shown in FIG. 2. Such oxygenators are supported in the sterilization chamber 1' during the sterilization operation. The apparatus shown in FIG. 2 includes components generally similar to those described in connection with the apparatus of FIG. 1.

Gas to be excited into plasma is supplied from the supplying tank 3 through the flowmeter 4, to a manifold 5' of the plasma generator. The amount of gas flow is indicated by the flowmeter pressure gauge 12 and the flow to the sterilization chamber can be initiated and terminated by operation of the shutoff valve 15. Flow of the gas plasma through the sterilization chamber 1' is induced by suction created by the vacuum pump 13. The connection between the sterilization chamber and the vacuum pump can be severed by closing valve 16 to avoid the necessity of stopping the vacuum pump between sterilizing operations. An oil trap 17 may be included in the suction line to pump 13, and a venting valve 18 for connecting the sterilization chamber 1' with atmosphere may be provided in the suction line to the vacuum pump.

Individual pipes 5" connect the manifold 5' to the individual oxygenators 2a, 2b and 2c, respectively. A radio-frequency field for converting the gas to plasma is produced by the exciters 6' in each of the gas supply pipes 5''. The radio-frequency field is created by such exciters connected to the radio-frequency generator 7, including an oscillator and an amplifier. The impedance matching network is adjusted by the radio-frequency tuner 8', and the power of the radio-frequency oscillator is indicated by the wattmeter 9'.

The blood oxygenators to be sterilized are shown in greater detail in FIGS. 3 and 4. A continuous flow of gas plasma is supplied past a regulating valve 19, shown in FIG. 2, to a pipe 20 leading to the interior of the oxygenator. In the arrangement shown in FIG. 3 the gas plasma is discharged from the interior of the oxygenator through the plasma exit 21 to the interior of sterilization chamber 1' shown in FIG. 2. The body of the oxygenator includes a multiplicity of capillary tubes 22 through which the gas plasma flows slowly to effect the sterilizing action. By such treatment bacteria is killed rather than being swept or scavenged from the surface of the article being sterilized. The resistance to flow of gas plasma through different oxygenators may vary, and the opening of valves 19 can be adjusted to equalize the flow effected through the oxygenators from the common manifold 5'.

Although it is only essential that the interiors of the capillary passages through the oxygenator be sterile because only such capillary passages come into contact with blood being oxygenated, it is desirable to have a completely sterilized oxygenator packaged in a sealed container to facilitate storage. It is therefore desirable to provide for flow of gas plasma over the exterior of the oxygenator at the same time that gas plasma is flowing through the capillary passages of the oxygenator.

FIG. 3 shows an enclosure 23 for the oxygenator having an inlet 24 and an outlet 25 for flow of gas plasma between the enclosure and the exterior of the oxygenator to the interior of the sterilization chamber 1' shown in FIG. 2. Such enclosure is sealed around the inlet 20 and the exit 21 for the gas plasma flowing through the interior of the oxygenator. If the enclosure 23 is in the form of a heat-sealable plastic bag and the tubes forming the openings 20 and 21 also are heat-sealable plastic, the openings 20, 21, 24 and 25 can all be sealed by pinching the walls of the tubes together and heat-sealing them closed to maintain the sterilized condition both of the interior and of the exterior of the oxygenator.

In the construction shown in FIG. 4 the gas plasma flows through the interior of the oxygenator 2' and then over the exterior of the oxygenator sequentially. In this instance the plasma exit 21' from the interior of the oxygenator discharges into the interior of the enclosure 23'. The gas plasma is then discharged from the interior of such enclosure, after passing over the exterior of the oxygenator, through the exit 25' to the interior of the sterilization chamber 1' shown in FIG. 2. With the use of such an arrangement it is necessary to close only the inlet passage 20 leading to the interior of the oxygenator, and the exit 25' leading from the enclosure 23'.

By providing continual flow of the gas plasma through the apparatus and over the surfaces of the article to be sterilized, the sterilizing operation is effected in a more efficient and expeditious manner. The sterilizing action of the gas plasma is also rendered more effective and consequently more expeditious by exposing the surfaces to be sterilized in a low pressure atmosphere, so that the gas plasma is more dense. The gas may be excited to form gas plasma by utilizing known techniques such as by subjecting it to a radio-frequency field as discussed above, by a technique such as described in the articles "Analytical Applications of Electrodelessly Discharged Gases" and "Research With Electrodelessly Discharged Gases" published in the periodical *Journal of Chemical Education*, Volume 43, Number 5, May 1966, and Number 6, June 1966, respectively, or by subjecting the gas to a condition comparable to that in a fluorescent light tube.

While the specific application of the sterilization process described above with respect to FIGS. 2, 3 and 4 relates to the sterilization of oxygenators, the process is particularly advantageous for the sterilization of various kinds of medical and hospital equipment in a sterilization chamber, including catheters of rigid silastic material, surgical tubing of rubber and polyvinyl chloride plastic, planchets of stainless steel or aluminum, scissors and scalpels. Plasma sterilization does not degrade the cutting edges of such implements. Glass microscope slides and membranes made of plastic material such as cellulose ester can also be sterilized in this way. Also prosthetic or body implant devices such as heart valves, pacemakers, joint and bone substitute components, and other artificial organs and components can be sterilized by the same process. Another important application of the process is for sterilization of enzymes such as lactic dehydrogenase, excrement or other waste material which must be stored for a time, such as in an airplane or a spacecraft, before being discarded. Such waste material may be ejected from a spacecraft and should be sterilized before ejection. In addition, the plasma process appears to have application for sterilizing fruits and vegetables and pharmaceutical preparations. The application would be particularly appropriate to prolong storage life.

The process may be used for decontamination of a spacecraft or components of it or spacecraft equipment. In such cases the plasma could be ejected from the plasma supply conduit 5 directly onto any portion of a space ship or space equipment in the rarefied atmosphere of outer space having a pressure of a few millimeters of mercury or less, such as being projected onto a scoop just before a sample of ground is taken from another celestial body to prevent the possibility of contaminating such celestial body with earth bacteria. Instead the article to be sterilized could be in a compartment of a space ship while being exposed to low pressure established by effecting communication between such compartment and outer space. Alternatively, the entire apparatus can be in the rarefied atmosphere of outer space or in the rarefied atmosphere of a space-simulation chamber.

We claim:

1. The process of sterilizing which comprises passing a substantially continuous flow of gas plasma to a space at subatmospheric pressure in contact with product not appreciably deteriorable by such gas plasma, and thereby sterilizing such product.

2. The process of sterilizing which comprises producing gas plasma from nonoxidizing gas, and passing a substantially continuous flow of such gas plasma to a space at subatmospheric pressure and in contact with product in such space and thereby sterilizing such product.

3. The process of sterilizing which comprises producing gas plasma from nonoxidizing gas and passing a substantially continuous flow of such gas plasma to a space at subatmospheric pressure and over a surface of an article in such space and thereby sterilizing such surface.

4. The process defined in claim 3, in which the space at subatmospheric pressure is outer space.

5. The process defined in claim 4, in which the surface to be sterilized is a portion of the exterior of a spaceship.

6. The process defined in claim 4, in which the surface to be sterilized is the surface of a scoop for scooping a ground sample from a celestial body.

7. The process of sterilizing a blood oxygenator having a plurality of capillary passages therethrough which comprises passing a substantially continuous flow of nonoxidizing gas plasma through such capillary passages while maintaining subatmospheric pressure in such passages.

8. The process defined in claim 7, including enclosing the oxygenator in a substantially evacuated chamber during such flow of gas plasma through its capillary passages.

9. The process defined in claim 8, and discharging gas plasma from the capillary passages of the oxygenator to the interior of the chamber exteriorly of the oxygenator.

10. The process of sterilizing which comprises passing a substantially continuous flow of gas plasma to a space at subatmospheric pressure and over a surface of an article in such space, said article being of material not appreciably deteriorable by such gas plasma, and thereby sterilizing such surface.

11. The process defined in claim 10, in which the flow of gas plasma is maintained for at least 1 minute.

12. The process defined in claim 10, in which the gas plasma flow is passed over the surface of an article in a compartment of a space ship, including establishing a low pressure in such compartment by effecting communication between such compartment and outer space.

13. The process defined in claim 10, including passing the substantially continuous flow of gas plasma over a surface of an article exposed to outer space and thereby sterilizing such surface.

14. The process defined in claim 10, including passing the flow of gas plasma over an interior surface and over an exterior surface of the article and thereby sterilizing such surfaces.

15. The process defined in claim 14, including passing the flow of gas plasma sequentially over the interior and exterior surfaces of the article.

16. Apparatus for sterilizing with gas plasma comprising a source of nonoxidizing gas, plasma generating means for ionizing gas from said source to form gas plasma, means for supplying the gas plasma to a blood oxygenator having capillary passages therethrough, and means for reducing the pressure in said capillary passages below atmospheric pressure for effecting a substantially continuous flow through such capillary passages of gas plasma generated by said plasma generating means.

17. The apparatus defined in claim 16, further comprising an enclosure for surrounding the blood oxygenator, and means for reducing the pressure in said enclosure below atmospheric pressure, the gas plasma supplying means supplying the gas plasma both to the interior of the oxygenator capillary passages and to the space between the exterior of the oxygenator and said enclosure.

18. The apparatus defined in claim 17, and means for discharge of gas plasma from the interior of the oxygenator to the interior of the enclosure surrounding the oxygenator.

* * * * *